US008383611B1

(12) United States Patent
Nagano et al.

(10) Patent No.: US 8,383,611 B1
(45) Date of Patent: Feb. 26, 2013

(54) CICLESONIDE CONTAINING AQUEOUS PHARMACEUTICAL COMPOSITION

(75) Inventors: Atsuhiro Nagano, Tokyo (JP); Yoshihisa Nishibe, Yamaguchi (JP); Kazuya Takanashi, Tokyo (JP)

(73) Assignee: Nycomed GmbH, Constance (DE)

( * ) Notice: Subject to any disclaimer, the term of this patent is extended or adjusted under 35 U.S.C. 154(b) by 0 days.

(21) Appl. No.: 10/110,632

(22) PCT Filed: Oct. 20, 2000

(86) PCT No.: PCT/JP00/07351
§ 371 (c)(1),
(2), (4) Date: Jul. 15, 2002

(87) PCT Pub. No.: WO01/28563
PCT Pub. Date: Apr. 26, 2001

(30) Foreign Application Priority Data

Oct. 20, 1999 (JP) .................................. 11/298186

(51) Int. Cl.
*A61K 31/58* (2006.01)
*A61K 31/56* (2006.01)
(52) U.S. Cl. ........................ 514/174; 514/179
(58) Field of Classification Search .................. 424/489, 424/401; 514/449, 461, 510, 937, 174, 179
See application file for complete search history.

(56) References Cited

U.S. PATENT DOCUMENTS

| 4,271,143 A | 6/1981 | Schoenwald et al. |
| 4,613,500 A | 9/1986 | Suzuki et al. |
| 4,615,697 A | 10/1986 | Robinson |
| 5,147,654 A | 9/1992 | Place et al. |
| 5,179,079 A | 1/1993 | Hansen et al. |
| 5,188,826 A | 2/1993 | Chandrasekaran et al. |
| 5,192,535 A | 3/1993 | Davis et al. |
| 5,200,195 A | 4/1993 | Dong et al. |
| 5,281,580 A | 1/1994 | Yamamoto et al. |
| 5,340,572 A | 8/1994 | Patel et al. |
| 5,393,773 A | 2/1995 | Craig et al. |
| 5,474,764 A | 12/1995 | Patel et al. |
| 5,474,768 A | 12/1995 | Robinson |
| 5,733,569 A | 3/1998 | Azria et al. |
| 5,869,096 A | 2/1999 | Barclay et al. |
| 5,942,242 A | 8/1999 | Mizushima et al. |
| 5,976,573 A | 11/1999 | Kim |
| 6,124,268 A * | 9/2000 | Ghosal ............... 514/27 |
| 6,288,049 B1 | 9/2001 | Morishima et al. |
| 6,291,445 B1 | 9/2001 | Nilsson et al. ............ 514/174 |
| 6,686,346 B2 | 2/2004 | Nilsson et al. ............ 514/174 |
| 6,767,901 B1 | 7/2004 | Nagano et al. |
| 6,939,559 B1 | 9/2005 | Nishibe et al. |
| 6,986,904 B2 | 1/2006 | Nilsson et al. ............ 424/489 |
| 2002/0077346 A1* | 6/2002 | Santus et al. ............ 514/412 |
| 2003/0008019 A1 | 1/2003 | Nishibe et al. |
| 2005/0181054 A1 | 8/2005 | Nishibe et al. |

FOREIGN PATENT DOCUMENTS

| CA | 2107587 A1 | 11/1992 |
| CA | 1332330 C | 9/1993 |
| CA | 1327314 C | 3/1994 |
| CA | 2164624 A1 | 1/1995 |
| CA | 2 268 140 C | 4/1998 |
| CA | 2 278 025 A1 | 7/1998 |
| EP | 0 209 247 A1 | 1/1987 |
| EP | 0 277 462 A1 | 8/1988 |
| EP | 298740 | 1/1989 |
| EP | 0 496 308 A1 | 7/1992 |
| EP | 560329 | 9/1993 |
| EP | 0 582 259 A2 | 2/1994 |
| EP | 0 781 546 A1 | 7/1997 |
| EP | 0843998 | 5/1998 |
| EP | 1 142 565 | 10/2001 |
| JP | 59-130820 A | 7/1984 |
| JP | 63-166832 A | 7/1988 |
| JP | 63-303931 A | 12/1988 |
| JP | 2-262526 A | 10/1990 |
| JP | 6-172199 A | 6/1994 |
| JP | 7-89857 | 4/1995 |
| JP | 7-188059 A | 7/1995 |
| JP | 8-217678 A | 8/1996 |
| JP | 9-25238 A | 1/1997 |
| JP | 9-235220 A | 9/1997 |
| JP | 11-21229 | 1/1999 |
| JP | 11-130658 | 5/1999 |
| JP | 11-130659 | 5/1999 |
| JP | 11-130660 | 5/1999 |
| RU | 2102979 C1 | 11/1998 |
| RU | 11829 | 12/2000 |
| WO | 92/14473 A1 | 9/1992 |
| WO | WO 95/11669 | 5/1995 |

(Continued)

OTHER PUBLICATIONS

Search Report from International Application No. PCT/JP00/07228.
Japanese Office Action mailed Jun. 1, 2004.
Russian Office Action with translation for PCT No. JP99/02126.
Chinese Office Action for Patent Application No. 9980085.0.
Dictionary of Food Additives, 1st edition, p. 49-50, and partial translation.
Abstract—Hussain, A., et al., "Nasal absorption of propranolol from different dosage forms by rats and dogs", *J Pharm Sci*, vol. 69, No. 12, pp. 1411-1413, (1980).
Abstract—Hussain, A.A., et al., "Nasal absorption of testosterone in rats", *J Pharm Sci*, vol. 73, No. 9, pp. 1300-1301, (1984).
Abstract—Hussain, A.A., et al., "The time of onset of action of sublingual nitroglycerin in exercise-induced angina pectoris. A methodological study", *Eur Heart J*, vol. 6, No. 7, pp. 625-630, (1985).
Abstract—Visor, G.C., et al., "Intranasal delivery of nicardipine in the rat", *J Pharm Sci*, vol. 75, No. 1, pp. 44-46, (1986).

(Continued)

*Primary Examiner* — Sreeni Padmanabhan
*Assistant Examiner* — Kara R McMillian
(74) *Attorney, Agent, or Firm* — Nath, Goldberg & Meyer; Joshua B. Goldberg; Sheldon M. McGee

(57) ABSTRACT

The present invention provides an aqueous pharmaceutical composition containing ciclesonide and hydroxypropyl-methylcellulose, wherein the ciclesonide is dispersed in an aqueous medium in the form of solid particles. The composition is able to avoid variations in the concentrations of ciclesonide during production as well as avoid decreases in the recovery rate of ciclesonide.

31 Claims, No Drawings

FOREIGN PATENT DOCUMENTS

| WO | WO 96/39143 | 12/1996 |
| --- | --- | --- |
| WO | 97/01337 A1 | 1/1997 |
| WO | 97/31626 A1 | 9/1997 |
| WO | 98/00178 A1 | 1/1998 |
| WO | WO 98/52542 | 11/1998 |
| WO | WO 99/25359 | 5/1999 |
| WO | 99/37286 A1 | 7/1999 |
| WO | WO 99/47144 | 9/1999 |
| WO | WO 99/53899 | 10/1999 |

OTHER PUBLICATIONS

Abstract—Ishikura T., et al., "Comparison of the metabolism of diltiazem following percutaneous, subcutaneous, oral and intravenous administration.", *Drug Des Deliv*, vol. 1, No. 2, pp. 151-156, (1986).

Abstract—Tukker, J.J., et al., "Comparison of bioavailability in man of tamoxifen after oral and rectal administration.", *J Pharm Pharmacol*, vol. 38, No. 12, pp. 888-892, (1986).

Abstract—Ritschel, W.A., "Absolute bioavailability of hydromorphone after peroral and rectal administration in humans: saliva/plasma ratio and clinical effects", *J Clin Pharmacol*, vol. 27, No. 9, pp. 647-653, (1987).

Abstract—Arnold, T.H., et al., "Pharmacodynamics of acute intranasal administration of verapamil: comparison with i.v. and oral administration.", *Biopharm Drug Dispos*, vol. 6, No. 4, pp. 447-454, (1985).

Abstract—Parab, P.V., et al., "Pharmacokinetics of hydromorphone after intravenous, peroral and rectal administration to human subjects.", *Biopharm Drug Dispos*, vol. 9, No. 2, pp. 187-199, (1988).

Abstract—Chang, S.F., et al., "Pharmacokinetics of bioavailability of hydromorphone: effect of various routes of administration.", *Pharm Res*, vol. 5, No. 11, pp. 718-721, (1988).

Abstract—Bawarshi-Nassar, R.N., et al., "Nasal absorption of 17-alpha-ethinyloestradiol in the rat.", *J Pharm Pharmacol*, vol. 41, No. 3, pp. 214-215, (1989).

Abstract—Kimura, R., et al., "Nasal absorption of tetraethylammonium in rats.", *Arch Int Pharmacodyn Ther*, vol. 302, pp. 7-17, (1989).

Abstract—Fossati, A., et al., "Pharmacokinetic study of neostigmine after intranasal and intravenous administration in the guinea pig.", *Drugs Exp Clin Res*, vol. 16, No. 11, pp. 575-579, (1990).

Abstract—Mintzer, M.J., "Asthma therapy: present trends and future prospects.", *Compr Ther*, vol. 16, No. 3, pp. 12-16, (1990).

Abstract—Harrison, L.I., et al., "Transdermal nitroglycerin systems: methods for comparison.", *Clin Ther*, vol. 13, No. 3, pp. 361-367, (1991).

Abstract—Hussain, M.A., et al., "Intranasal absorbtion of physostigmine and arecoline.", *J Pharm Sci*, vol. 890, No. 8, pp. 750-751, (1991).

Abstract—"A comparative evaluation of two transdermal nitroglycerin delivery systems: Nitro-Dur versus Transderm-Nitro. The collaborative Investigation Group.", *Clin Ther*, vol. 13, No. 5, pp. 545-549, (1991).

Abstract—Kraus, C., et al., "Pharmacokinetics and bioavailability of papaverine HCl following intravenous, peroral, rectal, vaginal, topical and buccal administration in begal dogs.", *Biopharm Drug Dispos*, vol. 12, No. 7, pp. 537-546, (1991).

Abstract—SHaaya, A.N., et al., "Pharmacokinetics and bioavailability of papaverine HCl after intravenous, intracorporeal and penis topical administration in beagle dogs.", *Methods Find Exp Clin Pharmacol*, vol. 14, No. 5, pp. 373-378, (1992).

Abstract—Yagi, N., et al., "Enhanced absorption of bumetanide from suppositories containing weak acids in rabbits.", *Biol Pharm Bull*, vol. 16, No. 3, pp. 263-267, (1993).

Abstract—Wang, J., et al., "Studies on the nasal absorption of gentamycin.", *Chung Hua Erh Pi Yen Hou Ko Tsa Chih*, vol. 29, No. 3, pp. 134-136, (1994).

Abstract—Cicinelli, E., et al., "Pharmacokinetics and endometrial effects of vaginal administration of mocronized progesterone in an oil-based solution to postmenopausal women.", *Fertil Steril*, vol. 65, No. 4, pp. 860-862, (1996).

Abstract—Pullan, R.D., "Colonic mucus, smoking and ulcerative colitis", *Ann R. Coll Surg Engl*, vol. 78, No. 2, pp. 85-91, (1996).

Abstract—Sato, H., et al., "Studies on the response of nitroglycerin oral spray compared with sublingual tablets for angina pectoris patients with dry mouth. A multicenter trial.", *Arzneimittelforschung*, vol. 47, No. 2, pp. 128-131, (1997).

Abstract—Farrar, J.T., et al., "Oral transmucosal fentayl citrate: randomized, double-blinded, placebo-controlled trial for treatment of breakthrough pain in cancer patients.", *J Natl Cancer Inst*, vol. 90, No. 8, pp. 611-616, (1998).

Machida, M., et al., "Effects of Surfactants and Protease Inhibitors on Nasal Absorption of Recombinant Human Granulocyte Colon-Stimulating Factor (rhG-CSF) in Rats", *Biol. Pharm. Bull*, vol. 17, No. 10, pp. 1375-1378, (1994).

Nomura, H., et al., "Effects of a Dosing Solution on the Nasal Absorption of Non-glycosylated Recombinant Human Granulocyte Colony-Stimulating Factor in Rats", *Biol. Pharm. Bull*, vol. 19, No. 10, pp. 1490-1493, (1996).

New Zealand Examination Report dated Aug. 31, 2001.

New Zealand Examination Report dated Oct. 23, 2001.

Bauer, K.H., et al., "Pharmazeutische Technologie", *Georg Thieme Verlag*, Stuttgart, $3^{rd}$ ed., p. 239 with translation.

European Office Action dated May 6, 2002—Supplemental Search Report.

European Office Action dated Apr. 14, 2004.

International Search Report for PCT/JP99/02126.

Derwent Publications Ltd. Week 199938 AN-1999-458604 XP002162689 "Fluorometholone eye drops suspension for treating inflammatory conditions".

* cited by examiner

CICLESONIDE CONTAINING AQUEOUS PHARMACEUTICAL COMPOSITION

FIELD OF INVENTION

The present invention relates to a ciclesonide-containing aqueous pharmaceutical composition for use in drug therapy that contains ciclesonide and hydroxypropylmethylcellulose, wherein said ciclesonide is dispersed in an aqueous medium in the form of solid particles. More particularly, the present invention relates to a ciclesonide-containing aqueous pharmaceutical composition having excellent ciclesonide dispersivity during production as compared with conventional aqueous pharmaceutical compositions.

BACKGROUND ART

Ciclesonide aqueous pharmaceutical compositions containing ciclesonide dispersed in an aqueous medium in a form of solid particles are expected to represent a useful drug form for reasons that include 1) it is not necessary to completely dissolve ciclesonide, 2) it can be directly administered to an affected site by spraying and so forth for treatment of local diseases such as those of the nasal mucosa, eyes and epidermis, and 3) they are easier to swallow than tablets or granule and so forth.

When present in an aqueous medium, ciclesonide is resistant to wetting and easily aggregates. The addition of wetting agent such as Polysorbate 80 and powerful stirring and so forth during production have been used in the prior art for the purpose of dispersing drug having such properties in an aqueous medium in a stable state.

Improvement of drug dispersivity of aqueous pharmaceutical compositions containing a drug dispersed in an aqueous medium in form of solid particles by addition of cellulose-based polymer is disclosed in Morishima et al. patent specification of WO99-37286. However, this patent relates to the redispersion of a drug that has settled during storage, and is fundamentally different from the present invention which relates to overcoming drawbacks of the migration of ciclesonide towards bubbles formed by powerful stirring during the production, and the adsorption of ciclesonide to the walls of the production apparatus. Moreover, the concentration of the cellulose-based polymer in the patent specification of Morishima et al. is 0.0001 to 0.003%, and methylcellulose can be used in place of hydroxypropylmethylcellulose for the cellulose-based polymer, while the addition of a nonionic surfactant is also required. It is not easy to deduce the present invention from this patent in which the optimum value of the hydroxypropylmethylcellulose concentration is from 0.01% w/w to 0.5% w/w, and does not require a surfactant.

DISCLOSURE OF THE INVENTION

During the course of production of ciclesonide aqueous pharmaceutical compositions, high shearing force is required to disperse ciclesonide and it is necessary to powerfully stir ciclesonide-containing aqueous pharmaceutical composition. Ciclesonide migrates to the bubbles formed at this time. Since this results in an increased concentration of ciclesonide in the upper portion of the ciclesonide aqueous pharmaceutical composition being higher than that in the lower portion, variation occurs in the ciclesonide concentration of ciclesonide aqueous pharmaceutical compositions produced. Moreover, the recovery rate decreases due to adsorption of ciclesonide to the walls and so forth of the production apparatus.

These variations in ciclesonide concentration and adsorption of ciclesonide to the production apparatus were hardly improved at all by the addition of wetting agents such as Polysorbate 80 that have been used in the prior art. Conversely, the amount of formed bubbles increases resulting in promotion of further variation in ciclesonide concentration.

Therefore, there is a considerable need for the development of a ciclesonide aqueous pharmaceutical composition that is able to avoid variations in ciclesonide concentrations during production as well as the decrease in ciclesonide recovery rate.

Namely, the object of the present invention is to provide a ciclesonide aqueous pharmaceutical composition that avoids variations in ciclesonide concentration during production as well as decreases in the ciclesonide recovery rate.

As a result of earnest studies to solve the above problems, the inventors of the present invention found that a ciclesonide aqueous pharmaceutical composition can be provided that avoids variations in ciclesonide concentrations during production as well as decreases in the ciclesonide recovery rate, by using a ciclesonide aqueous pharmaceutical composition containing ciclesonide and hydroxypropylmethylcellulose, thereby leading to completion of the present invention.

Namely, the present invention relates to an aqueous pharmaceutical composition containing ciclesonide and hydroxypropylmethylcellulose, wherein said ciclesonide is dispersed in an aqueous medium in form of solid particles.

EMBODIMENT FOR CARRYING OUT THE INVENTION

It is essential that composition of the present invention contain ciclesonide, while water-soluble, water-low soluble or water-insoluble drugs other than ciclesonide can be added. Specific examples of these include vasoconstrictors, bronchodilators, anti-allergic agents and expectorants.

Although the ciclesonide particles that can be used in the present invention may be of any size, they are preferably within the range of 10 nm to 100 μm, and particularly preferably within the range of 10 nm to 10 μm.

Although any substances may be used for the water-insoluble or water-low soluble substance that can be used in the present invention, a preferable example is a cellulose, and a particularly preferable example is crystalline cellulose.

In the present invention, the concentration of water-insoluble substance and/or water-low soluble substance present in form of solid particles in an aqueous medium is preferably 0.3% w/w and above, and particularly preferably 1% w/w to 10% w/w, relative to the total amount of the composition.

In addition, an aqueous polymer substance can also be added in the present pharmaceutical composition. Specific examples of such include propylene glycol alginate, pectin, low methoxyl pectin, gua gum, gum arabic, carrageenan, methylcellulose, carboxymethylcellulose sodium, xanthan gum and hydroxypropylcellulose, while particularly preferable examples include carboxymethylcellulose sodium, polyethylene glycol and hydroxypropylcellulose. In addition, crystalline cellulose carmellose sodium, is an example of a combination of these water-soluble substances and water-insoluble substances that can be used in the present invention, and it consists of a mixture of carboxymethylcellulose sodium and crystalline cellulose. Furthermore, in the case of adding these water-soluble polymer substances, the concentration of said substance is preferably 1% w/w to 30% w/w relative to the water-insoluble substance and/or water-low soluble substance.

The ciclesonide-containing aqueous pharmaceutical composition of the present invention is also required to contain hydroxypropylmethylcellulose. Although this may be of any grade, a specific example is hydroxypropylmethylcellulose 2910.

Although said hydroxypropylmethylcellulose may be present at any concentration, its concentration is preferably from 0.01% w/w to 30% w/w, particularly preferably from 0.01% w/w to 5% w/w, more particularly preferably from 0.01% w/w to 1% w/w, and most preferably from 0.01% w/w to 0.5% w/w, relative to the total amount of composition.

A wetting agent, although not essential in the present invention, can be added, specific examples of which include Polysorbate 80, glycerin monostearate, polyoxyl stearate, lauromacrogol, sorbitan oleate and sucrose fatty acid esters.

In the present invention, a substance for controlling osmotic pressure (osmotic pressure-controlling agent) can be added to control osmotic pressure, specific examples of which include salts such as sodium chloride and water-soluble sugars such as glucose, with glucose being a particularly preferable example.

An effective amount of ciclesonide used in the present invention can be determined according to the type and degree of the respective disease, as well as the age and body weight of the patient, and so forth.

The concentration of ciclesonide of the present invention is preferably from 0.01% w/w to 1% w/w, and particularly preferably from 0.05% w/w to 0.5% w/w, relative to the total amount of the composition.

Any method for dispersing a water-insoluble substance and/or water-low soluble substance in an aqueous medium may be used for the production of the ciclesonide-containing aqueous pharmaceutical composition in the present invention, a specific example of which is a method that uses a homomixer.

Known antiseptics, pH controlling agents, preservatives, buffers, colorants, smell corrigents and so forth may be added as necessary to the composition of the present invention to improve its physical properties, appearance or odor and so forth of the formulation. Examples of antiseptics include benzalkonium chloride, examples of pH controlling agents include hydrochloric acid and sodium hydroxide, examples of preservatives include ascorbic acid, examples of buffers include phosphoric acid and its salt, examples of colorants include red dye no. 2, and examples of smell corrigents include menthol.

According to the present invention as described above, a ciclesonide aqueous pharmaceutical composition is provided that avoids variations in ciclesonide concentration during production as well as decreases in the recovery rate of ciclesonide more effectively than aqueous pharmaceutical compositions of the prior art. These effects also lead to improved quality as well as decreased production cost due to the higher recovery rate.

Thus, the present invention has extremely high significance in terms of both quality and economy for the production of ciclesonide aqueous pharmaceutical compositions.

EXAMPLES

The following provides an explanation of the present invention through its Examples.

Ciclesonide used in the present invention was manufactured by Byk Gulden Co., the crystalline cellulose carmellose sodium by Asahi Chemical Industry Co., Ltd. (Avicel™ RC-A591NF), hydroxypropylmethylcellulose 2910 by Shin-Etsu Chemical Co., Ltd. (TC-5RW™ or Metrose 60SH-4000™), Polysorbate 80 by Nippon Surfactant Co., Ltd., and the sorbitan trioleate by Nikko Chemical Co., Ltd. ROBOMICS™ manufactured by Tokushu Kika Kogyo Co., Ltd. was used for the homomixer.

Example 1

Ciclesonide aqueous pharmaceutical compositions containing the components indicated below were prepared on a 300 ml scale by processing with a homomixer. Homomixer processing was performed at 6000 rpm for 30 minutes.

Composition (1)
Ciclesonide: 0.1% w/w
Crystalline cellulose carmellose sodium: 1.7% w/w
Hydroxypropylmethylcellulose 2910 (TC-5RW™): 0.01% w/w Composition (2)
Ciclesonide: 0.1% w/w
Crystalline cellulose carmellose sodium: 1.7% w/w
Hydroxypropylmethylcellulose 2910 (TC-5RW™): 0.1% w/w Composition (3)
Ciclesonide: 0.1% w/w
Crystalline cellulose carmellose sodium: 1.7% w/w
Hydroxypropylmethylcellulose 2910 (TC-5RW™): 1% w/w Composition (4)
Ciclesonide: 0.1% w/w
Crystalline cellulose carmellose sodium: 1.7% w/w
Hydroxypropylmethylcellulose 2910 (Metrose 60SH-4000™): 0.01% w/w Composition (5)
Ciclesonide: 0.1% w/w
Crystalline cellulose carmellose sodium: 1.7% w/w
Hydroxypropylmethylcellulose 2910 (Metrose 60SH-4000™): 0.1% w/w Immediately after processing compositions 1 to 5 with the homomixer, the ciclesonide aqueous pharmaceutical compositions were collected from the upper and lower portions of the emulsification tank, followed by quantification of the ciclesonide concentrations by HPLC. The value for the upper portion of the emulsification tank was calculated by taking the ciclesonide concentration in the lower portion of the emulsification tank to be 100%.

Subsequently, the ciclesonide concentrations of the ciclesonide aqueous pharmaceutical compositions recovered from the emulsification tank were quantified by HPLC, and the ciclesonide recovery rates were determined based on the theoretical value of the ciclesonide concentration as calculated from the charged amount.

Those values are shown in Table 1.

Comparative Example 1

Ciclesonide aqueous pharmaceutical compositions containing the components indicated below were prepared on a 300 ml scale by processing with a homomixer. Homomixer processing was performed at 6000 rpm for 30 minutes.

Composition (6)
Ciclesonide: 0.1% w/w
Crystalline cellulose carmellose sodium: 1.7% w/w
Polysorbate 80: 0.1% w/w Composition (7)
Ciclesonide: 0.1% w/w
Crystalline cellulose carmellose sodium: 1.7% w/w
Sorbitan trioleate: 0.1% w/w Immediately after processing compositions 6 and 7 with the homomixer, the ciclesonide aqueous pharmaceutical compositions were collected from the upper and lower portions of the emulsification tank, followed by quantification of the ciclesonide concentrations by HPLC. The value for the upper portion of the emulsification tank was calculated by taking the ciclesonide concentration in the lower portion of the emulsification tank to be 100%.

Subsequently, the ciclesonide concentrations of the ciclesonide aqueous pharmaceutical compositions recovered from the emulsification tank were quantified by HPLC, and the ciclesonide recovery rates were determined based on the theoretical value of the ciclesonide concentration as calculated from the charged amount.

Those values are shown in Table 1.

TABLE 1

|  |  | Ciclesonide concentration immediately after processing (%) | | |
| --- | --- | --- | --- | --- |
|  | Preparation | Upper portion of emulsification tank | Lower portion of emulsification tank | Recovery rate (%) |
| Embodiment 1 | Composition 1 | 138.1 | 100.0 | 104.2 |
|  | Composition 2 | 100.3 | 100.0 | 100.7 |
|  | Composition 3 | 99.6 | 100.0 | 101.5 |
|  | Composition 4 | 147.9 | 100.0 | 98.4 |
|  | Composition 5 | 100.4 | 100.0 | 100.8 |
| Comparative | Composition 6 | 131.1 | 100.0 | 78.2 |
| Example 1 | Composition 7 | 438.7 | 100.0 | 43.0 |

In the case of compositions 2, 3 and 5, which contained 0.1 to 1% w/w of hydroxypropylmethylcellulose 2910, the ciclesonide concentrations in the emulsification tank immediately after homomixer processing were uniform, and the recovery rates were almost 100%. In addition, in the case of compositions 1 and 4, which contained 0.01% w/w of hydroxypropylmethylcellulose 2910, although the ciclesonide concentrations in the emulsification tank immediately after homomixer processing were somewhat non-uniform, the recovery rates were almost 100%. In contrast, in the case of composition 6, which contained 0.1% w/w of Polysorbate 80, the ciclesonide concentration in the upper portion of the emulsification tank immediately after homomixer processing was more than 30% higher than in the lower portion. In addition, the recovery rate decreased by about 20%. In the case of composition 7, which contained 0.1% w/w of sorbitan trioleate, the ciclesonide concentration in the upper portion of the emulsification tank immediately after homomixer processing was more than 40% higher than in the lower portion, and the recovery rate decreased by more than half.

Based on these results, it was determined that the use of a composition containing hydroxypropylmethylcellulose made it possible to avoid variation in the concentration of ciclesonide during production as well as avoid a decrease in the recovery rate of ciclesonide.

The invention claimed is:

1. An aqueous pharmaceutical composition which comprises ciclesonide, crystalline cellulose carmellose sodium and hydroxypropylmethylcellulose, wherein said ciclesonide is uniformly dispersed in an aqueous medium in the form of solid particles, wherein said crystalline cellulose carmellose sodium concentration is 1.7% w/w, and wherein said hydroxypropylmethylcellulose concentration is 0.1% w/w, relative to the total amount of the composition.

2. An aqueous pharmaceutical composition according to claim 1 which further comprises one or more types of a water-insoluble substance and/or water-low soluble substance which is one or more types of cellulose.

3. An aqueous pharmaceutical composition according to claim 2, which further comprises a water-soluble polymer substance.

4. An aqueous pharmaceutical composition according to claim 3, wherein said water-soluble polymer substance is one or more types selected from the group consisting of polyethylene glycol, propylene glycol alginate, pectin, methoxyl pectin, guar gum, gum arabic, carrageenan, methylcellulose, xanthan gum and hydroxypropylcellulose.

5. An aqueous pharmaceutical composition according to claim 3, wherein said water-soluble polymer substance is polyethylene glycol.

6. An aqueous pharmaceutical composition according to claim 3, wherein said water-soluble polymer substance is hydroxypropylcellulose.

7. An aqueous pharmaceutical composition according to claim 1 which further comprises a water-soluble polymer substance.

8. An aqueous pharmaceutical composition according to claim 7, wherein said water-soluble polymer substance is one or more types selected from the group consisting of polyethylene glycol, propylene glycol alginate, pectin, methoxyl pectin, guar gum, gum arabic, carrageenan, methylcellulose, xanthan gum and hydroxypropylcellulose.

9. An aqueous pharmaceutical composition according to claim 7, wherein said water-soluble polymer substance is polyethylene glycol.

10. An aqueous pharmaceutical composition according to claim 7, wherein said water-soluble polymer substance is hydroxypropylcellulose.

11. An aqueous pharmaceutical composition according to claim 1, wherein the ciclesonide particles have a size of between about 10 nm and about 100 μm.

12. An aqueous pharmaceutical composition according to claim 1, wherein the ciclesonide particles have a size of between about 10 nm and about 10 μm.

13. An aqueous pharmaceutical composition according to claim 1, further comprising at least one wetting agent.

14. An aqueous pharmaceutical composition according to claim 13, wherein at least one wetting agent present is selected from the group consisting of Polysorbate 80, glycerin monostearate, polyoxyl stearate, lauromacrogol, sorbitan oleate and sucrose fatty acid esters.

15. An aqueous pharmaceutical composition according to claim 1, further comprising at least one osmotic-pressure controlling agent.

16. An aqueous pharmaceutical composition according to claim 15, wherein at least one osmotic-pressure controlling agent present is a salt.

17. An aqueous pharmaceutical composition according to claim 16, wherein the salt is sodium chloride.

18. An aqueous pharmaceutical composition according to claim 15, wherein at least one osmotic-pressure controlling agent present is a water-soluble sugar.

19. An aqueous pharmaceutical composition according to claim 18, wherein the water-soluble sugar is glucose.

20. An aqueous pharmaceutical composition according to claim 1, wherein the ciclesonide is present in a concentration of between about 0.01% w/w and about 1% w/w, relative to the total amount of the composition.

21. An aqueous pharmaceutical composition according to claim 1, wherein the ciclesonide is present in a concentration of between about 0.05% w/w and about 0.5% w/w, relative to the total amount of the composition.

22. An aqueous pharmaceutical composition according to claim 1, further comprising at least one antiseptic.

23. An aqueous pharmaceutical composition according to claim 22, wherein at least one antiseptic present is benzalkonium chloride.

24. An aqueous pharmaceutical composition according to claim 1, further comprising at least one pH controlling agent.

25. An aqueous pharmaceutical composition according to claim 24, wherein at least one pH controlling agent present is selected from the group consisting of hydrochloric acid and sodium hydroxide.

26. An aqueous pharmaceutical composition according to claim 1, further comprising at least one preservative.

27. An aqueous pharmaceutical composition according to claim 26, wherein at least one preservative present is ascorbic acid.

28. An aqueous pharmaceutical composition according to claim 1, further comprising at least one buffer.

29. An aqueous pharmaceutical composition according to claim 28, wherein at least one buffer present is selected from the group consisting of phosphoric acid and salts thereof.

30. An aqueous pharmaceutical composition according to claim 1, further comprising
   (a) at least one pH controlling agent, and
   (b) at least one antiseptic or at least one preservative.

31. An aqueous pharmaceutical composition according to claim 24, wherein the at least one pH controlling agent is hydrochloric acid.

* * * * *